(12) United States Patent
Fehre et al.

(10) Patent No.: US 10,674,979 B2
(45) Date of Patent: Jun. 9, 2020

(54) MOBILE C-ARM SYSTEM

(71) Applicants: Jens Fehre, Hausen (DE); Alexander Gemmel, Erlangen (DE); Andreas Limmer, Fürth (DE); Ralf Nanke, Neunkirchen am Brand (DE)

(72) Inventors: Jens Fehre, Hausen (DE); Alexander Gemmel, Erlangen (DE); Andreas Limmer, Fürth (DE); Ralf Nanke, Neunkirchen am Brand (DE)

(73) Assignee: Siemens Healthcare GmbH, Erlangen (DE)

( * ) Notice: Subject to any disclaimer, the term of this patent is extended or adjusted under 35 U.S.C. 154(b) by 65 days.

(21) Appl. No.: 15/764,558

(22) PCT Filed: Aug. 9, 2016

(86) PCT No.: PCT/EP2016/068926
§ 371 (c)(1),
(2) Date: Mar. 29, 2018

(87) PCT Pub. No.: WO2017/054975
PCT Pub. Date: Apr. 6, 2017

(65) Prior Publication Data
US 2018/0279981 A1    Oct. 4, 2018

(30) Foreign Application Priority Data
Sep. 30, 2015   (DE) .................. 10 2015 218 922

(51) Int. Cl.
*A61B 6/00*    (2006.01)

(52) U.S. Cl.
CPC .......... *A61B 6/4476* (2013.01); *A61B 6/4405* (2013.01); *A61B 6/4441* (2013.01)

(58) Field of Classification Search
CPC .... A61B 6/4405; A61B 6/4441; A61B 6/4476
See application file for complete search history.

(56) References Cited

U.S. PATENT DOCUMENTS 6,131,690 A    10/2000  Galando et al.
8,177,430 B2   5/2012   Bouvier
(Continued)

FOREIGN PATENT DOCUMENTS

DE    29517922 U1    1/1996
DE    10111800 A1    10/2002
(Continued)

OTHER PUBLICATIONS

German Office Action for German Application No. 102015218922.8, dated May 18, 2016.
(Continued)

*Primary Examiner* — David P Porta
*Assistant Examiner* — Fani Boosalis
(74) *Attorney, Agent, or Firm* — Lempia Summerfield Katz LLC

(57) ABSTRACT

The invention relates to a mobile C-arm system (C1), at least comprising at least three wheels, at least two wheels each having an electric motor, wherein the electric motor has a stator (S) and a rotor (R), the stator (S) being connected to a wheel suspension (T) of the wheel and the rotor (R) being surrounded peripherally by a running wheel (L).

20 Claims, 2 Drawing Sheets

(56) References Cited

U.S. PATENT DOCUMENTS

| | | |
|---|---|---|
| 8,374,937 B2 | 2/2013 | Arnott et al. |
| 8,666,585 B2 | 3/2014 | Bouvier |
| 10,271,802 B2* | 4/2019 | Wendlandt ............. A61B 6/105 |
| 2002/0150214 A1 | 10/2002 | Spahn |
| 2012/0161675 A1 | 6/2012 | Ding et al. |
| 2012/0219122 A1 | 8/2012 | Herrmann |

FOREIGN PATENT DOCUMENTS

| | | |
|---|---|---|
| DE | 10118745 A1 | 10/2002 |
| DE | 102011057074 A1 | 6/2012 |
| DE | 102011004667 B4 | 7/2014 |
| WO | 0150959 A1 | 7/2001 |

OTHER PUBLICATIONS

PCT International Search Report and Written Opinion of the International Searching Authority dated Oct. 27, 2016, for corresponding PCT/EP2016/068926.

* cited by examiner

MOBILE C-ARM SYSTEM

CROSS REFERENCE TO RELATED APPLICATIONS

The present patent document is a § 371 nationalization of PCT Application Serial Number PCT/EP2016/068926, filed Aug. 9, 2016, designating the United States, which is hereby incorporated by reference in its entirety. This patent document also claims the benefit of DE 102015218922.8, filed on Sep. 30, 2015, which is also hereby incorporated by reference in its entirety.

FIELD

Embodiment provide a mobile C-arm system including at least three wheels, where at least two wheels of the at least three wheels each have an electric motor.

BACKGROUND

Mobile X-ray devices in the form of C-arm devices are used, for example, for intraoperative imaging in operational deployment. The devices are positioned precisely in relation to the patient to be treated prior to each deployment. The devices may be equipped with wheels, on which the devices may be displaced manually. The wheels may be driven in a motorized manner to enable the displacement of the devices with less or without any exertion of force and to automate movements of the devices for clinical applications.

A C-arm system with three wheels is known from U.S. Pat. No. 6,374,937 B1, where two of the wheels are each connected to a drive and are mounted such that the wheels may be pivoted about a vertical axis. A third wheel is implemented in a freely movable manner. Using the driven wheels, a movement of the C-arm system along a direction (e.g., in parallel with a patient couch) may be controlled. The pivoting of the wheels about the vertical axis is possible between a first and a second position. The drives of the wheels are arranged in a base unit or a lower chassis of the C-arm system.

Similar C-arm systems are known from U.S. Pat. No. 8,666,582 B2, U.S. Pat. No. 8,177,430 B2 and EP 1 246 566 B1.

A frequently recurring problem in clinical applications is adopting directions of movement with the mobile C-arm system (e.g., a movement in the opposite direction). Examples include when the C-arm system is moved backwards, to the side, or diagonally away from the examination couch, or to create space for an operating surgeon. Subsequently, the C-arm system may be reversed into an original position on the examination couch again. In the "park & return" example, the mobility and the steering of the wheels are implemented so that a precise reversal of the previous movement is possible.

Another example is "stitching" (e.g., when a panoramic recording of the patient is to be compiled). The C-arm is first moved by the user along the patient couch without imaging to avoid collisions in the actual operating mode and to define the start and end point of the recording. For the panoramic recording, the movement of the C-arm in the precise opposite direction is performed. The steering of the wheels is implemented such that a precise reversal of the previous direction is possible.

A further example includes a C-arm system without isocentric geometry. The object to be imaged is kept in the center of the image during a change in the orbital angle that is possible by a change in the lifting column position and the wheel position. During a constant shift in the imaging position, the orientation of the wheels of the C-arm system are held precisely to provide a precisely equal movement in the opposite direction.

SUMMARY AND DESCRIPTION

The scope of the present invention is defined solely by the appended claims and is not affected to any degree by the statements within this summary. The present embodiments may obviate one or more of the drawbacks or limitations in the related art.

Embodiments provide a C-arm system that provides precise positioning capability and direction reversal of movements.

The mobility of a C-arm system may be improved by driving each wheel individually with the drive mechanism integrated into the wheel. The wheels may be driven by electric motors (e.g., hub motors with rotor and stator), and may be implemented as components of the wheels.

The C-arm system may include two wheels that are steerable and driven in a motorized manner, and at least one further wheel that may move freely, but is not necessarily motorized. Using the steering, an orientation of the wheels may be implemented about a vertical axis. A driven movement of the wheels is affected as a rotation about a horizontal wheel center axis. The steering of the wheels may be locked in any direction. The locking provides at least one definition of the main movement axes (e.g., forward/backward and left/right), but also a locking in all other directions (e.g., sleeplessly or in intermediate steps of 5° in each case). To prevent the C-arm system from veering off during the movement in an opposite direction, the at least one further wheel is either also steerable and lockable, or suspended such that the one further wheel follows the direction of the driven wheels smoothly.

The wheels may be rotated individually and/or in opposite directions to allow the C-arm system to travel around curves flexibly. The wheels may be steerable independently. Rotations of the C-arm system about a vertical device axis are allowed. By rotating the wheels in opposite directions, a rotation about any desired vertical axis may be realized. The axis of rotation is located in the immediate vicinity of the C-arm or the patient, the movement of which is referred to as a swivel movement, as depicted in the patent specification DE 10 2011 004 667 B4, for example. Two wheels oriented in parallel and steered in opposite directions may provide a braking of the C-arm system that provides an advantage on inclined planes.

In an embodiment, a mobile C-arm system that includes at least three wheels is provided. Each of the at least two wheels includes an electric motor. The electric motor includes a stator and a rotor with the stator connected to a wheel suspension of the wheel and the rotor circumferentially surrounded by a running wheel. Electromagnets are arranged in the stator of the electric motor, and permanent magnets are arranged in the rotor of the electric motor. At least one wheel is a non-driven wheel. The C-arm system provides a motorized and non-motorized positioning and a precise movement in an opposite direction.

The C-arm system includes a lower chassis (e.g., a base unit), on which the at least three wheels are arranged. In an embodiment, the C-arm system includes exactly three wheels. Three wheels (e.g., representing a triangular base or standing area of the C-arm system) provide increased stability (e.g., in a scenario with unevenness of the ground). At least two of the wheels include an electric motor. The electric motor includes a rotor and a stator in each case. In an embodiment, the electric motor is integrated into the wheel in each case. The stator is connected to a wheel suspension of the wheel, and the rotor is circumferentially surrounded by a running wheel. The connection between stator and a wheel suspension or a support frame of the base unit may be both flexible and movable, or rigid. The circumferential running wheel of the stator provides the contact surface of the wheel. Rolling elements or roller bearings are arranged between the rotor and stator, for example, in the form of balls, pins, or rollers.

In an embodiment, at least one further wheel is provided in a freely movable manner. The wheel is both freely movable about a horizontal wheel center axis (e.g., without a drive), and may also be flexibly pivoted and thus oriented about a vertical axis. In an embodiment, at least one wheel is provided as a non-driven wheel. An omni wheel may refer to a wheel, the contact surface of which includes a plurality of rollers. The axes of rotation thereof are each at right angles to the axis of rotation of the main wheel. The omni wheel may be displaced or rolled both in a radial and in an axial direction as a result. Omni wheels are also referred to as omnidirectional wheels or all-side wheels. In an embodiment with three wheels, two wheels are provided as omni wheels and one wheel as a freely movable, conventional running wheel.

The electric motors may be hub motors. The hub motors are directly built into the wheels and support the wheel hub. The generated torque is directly transferred to the wheel by the electric motor by the stator and rotor. In an embodiment, the electric motor is a direct current (DC) motor. A plurality of electromagnets may be arranged in the stator in the form of coils. A plurality of permanent magnets may be arranged in the rotor.

In an embodiment of the C-arm system, a control apparatus (e.g., a controller) that is connected to each of the wheels individually is provided. The wheels of the C-arm system may be actuated individually in terms of direction of movement, orientation, and speed of the wheels and thus provide a precise positioning of the device. By rotating two wheels aligned in parallel in opposite direction, a braking movement of the C-arm system is possible.

The control apparatus may include a control loop that regulates the speed of each wheel individually. The regulation of the speed may be affected both with regard to the rotational speed about the horizontal wheel center axis to move forward, and also with regard to the rotational speed about a vertical axis to orient the wheel and change the direction of movement of the C-arm system.

A steering may orient and pivot the wheels about a vertical axis that actuates the wheels individually in each case. The steering may be locked individually for each wheel. In an embodiment, the wheels are configured to be locked continuously or steplessly. Another embodiment provides for the wheels to be configured to be locked at discrete angular increments. For example, angular increments of 45°, 30°, 15°, or 5° may be implemented. The steering may be a girth gear unit with at least two interlocking gear rings. For example, the support frame of the wheel may be mounted such that the support frame may be rotated on the base unit by the girth gear unit.

In an embodiment, the C-arm system further includes an autonomous power supply to the wheels (e.g., the electric motor for driving the wheels). The power supply may include a battery and/or a fuel cell. A charging apparatus may be provided for charging the power supply. The charging apparatus may, for example, provide for contactless charging of the power supply (e.g., inductively). The charging apparatus may provide for charging the power supply by a cable connection, for example, by a charging cable.

DETAILED DESCRIPTION

Figure 1:
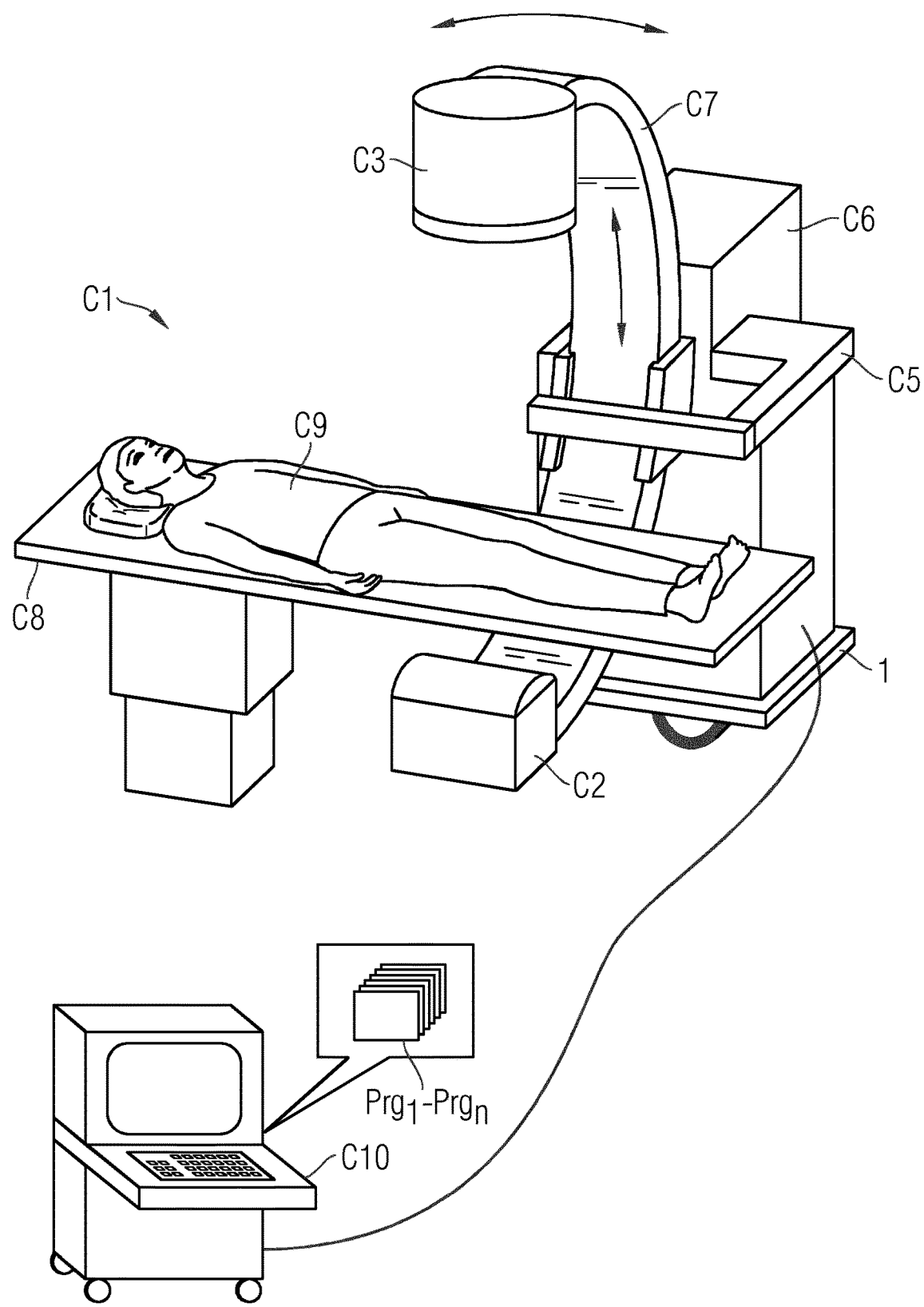
FIG. 1 depicts an embodiment of a C-arm device with a displaceable base unit.
Figure 2:
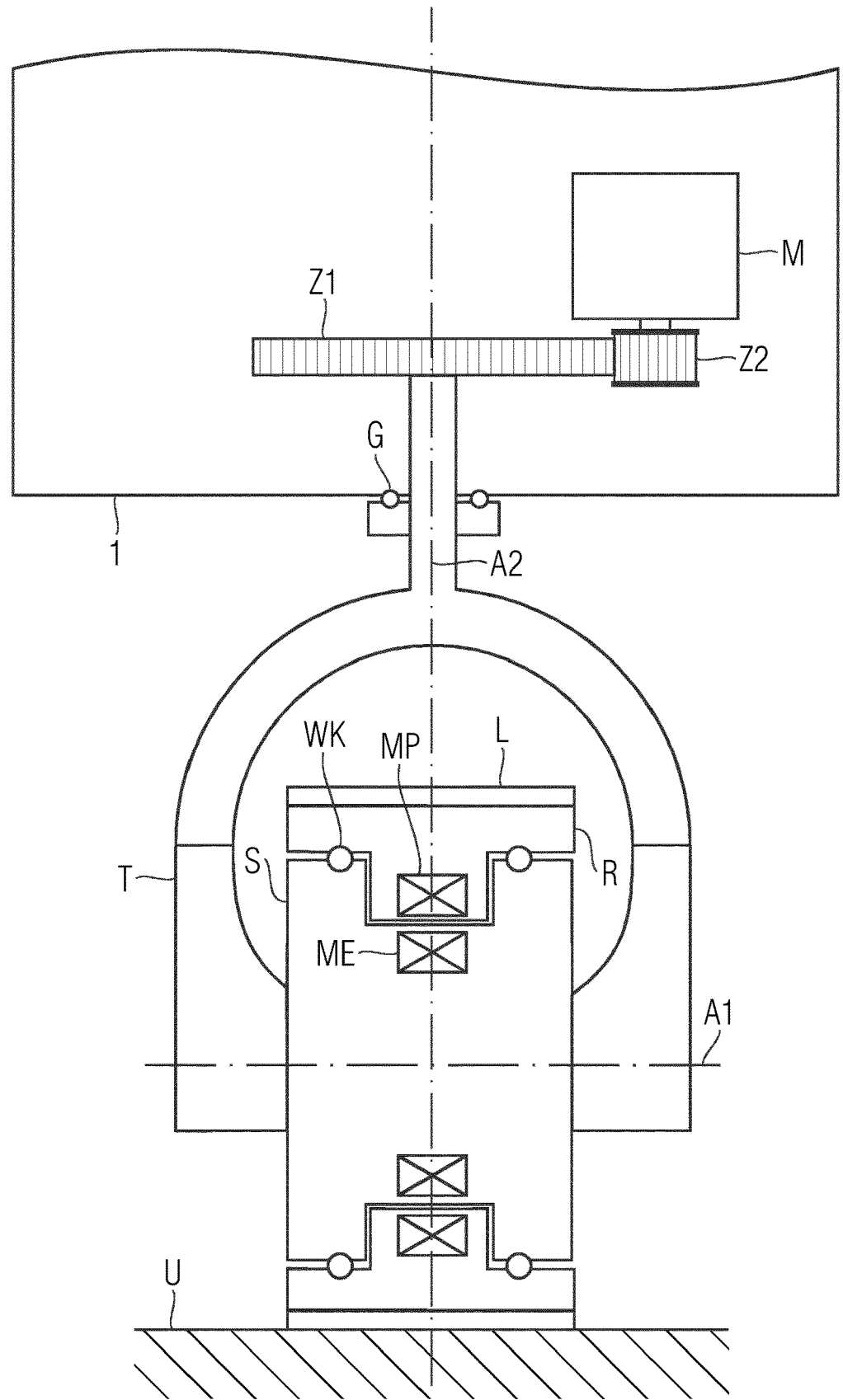
FIG. 2 depicts a vertical cross-section in the plane of the axes through a wheel according to an embodiment including an integrated electric motor.

FIGS. 1 and 2 depict: 1: base unit; A1: first axis/horizontal wheel center axis; A2: second axis/vertical pivot axis; C1: C-arm device; C2: X-ray tube; C3: detector; C5: support arm; C6: housing; C7: C-arm; C8: patient couch; C9: patient; C10: control and computing system; G: bearing; L: contact surface; M: motor: ME: electromagnet; MP: permanent magnet; R: rotor; S: stator; T: support frame; U: ground; WK: rolling element; Z1, Z2: gear ring; and Prg1-Prgn: computer programs.

FIG. 1 depicts a mobile C-arm device C1 according to an embodiment. The C-arm device C1 includes a housing C6, in which a control and computing system C10 is located with computer programs Prg1-Prgn stored thereon and with a display (not visible in this view). Fastened to the housing C6 is a displaceable support arm C5 that supports a C-arm C7 that may carry out both an orbital rotation and an angular rotation. Fastened to one end of the C-arm C7 is an X-ray tube C2, that may emit a variable radiation beam during operation. Attached opposite at the other end of the C-arm C7 is a detector C3. Arranged in the beam path between X-ray tube C2 and detector C3 is a patient C9 located on a patient couch C8.

In an embodiment, the C-arm device C1 also includes the base unit 1 with three wheels, to which the housing C6 is fastened. Using the base unit 1, the device may be displaced and positioned in a simple manner.

FIG. 2 depicts a wheel according to an embodiment with an integrated electric motor. A vertical section in the plane spanned by the horizontal axis A1 and the vertical axis A2 is depicted. The wheel includes a support frame T that is fastened to the base unit 1 of the C-arm system and mounted in a movable manner to the base unit 1 by the bearing G. To steer or orient the wheel, the girth gear unit of the wheel includes a motor M. The girth gear unit includes two interlocking gear rings Z1 and Z2. The orientation of the wheel is effected by the movement of the gear rings Z1 and Z2 in opposite directions. The steering, (e.g., the orientation) of the wheel may be locked in any manner by fixing the gear rings Z1 and Z2 against one another.

In the lower part, the support frame T is connected to the electric motor of the wheel (e.g., connected to the stator S of the electric motor). The electric motor includes a stator S and a rotor R. The rotor R is mounted about the stator S. A plurality of permanent magnets MP are accommodated in the rotor R, and a plurality of electromagnets ME that induce the electric drive are accommodated in the stator S. Arranged between rotor R and stator S are spherical rolling elements WK. The rotor R is also surrounded circumferentially by a running wheel or a contact surface L that may, for example, include rubber or plastic and provides an improved gripping of the wheel to the ground.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

While the present invention has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A mobile C-arm system comprising:
   a C-arm; and
   at least three wheels connected to the C-arm, wherein at least two wheels of the at least three wheels each include an electric motor, and at least one wheel of the at least three wheels is a non-driven wheel;
   wherein at least one of the electric motors comprises a stator and a rotor,
   wherein the stator is connected to a wheel suspension of a wheel of the at least two wheels and the rotor is circumferentially surrounded by a running wheel,
   wherein one or more electromagnets are arranged in the stator of the electric motor, and one or more permanent magnets are arranged in the rotor of the respective electric motor.

2. The mobile C-arm system of claim 1, at least one wheel of the at least three wheels is freely movable.

3. The mobile C-arm system of claim 2 further comprising:
   a controller connected to each of the at least two wheels individually.

4. The mobile C-arm system of claim 3, wherein the controller comprises a control loop configured to regulate a speed of each wheel of the at least two wheels individually.

5. The mobile C-arm system of claim 3, further comprising:
   a steering configured to pivot the at least three wheels about a vertical axis,
   wherein the steering is configured to actuate each of the at least three wheels individually.

6. The mobile C-arm system of claim 5, wherein the steering is configured to be lockable individually for each wheel of the at least three wheels.

7. The mobile C-arm system of claim 1, wherein the at least one electric motor is a hub motor.

8. The mobile C-arm system of claim 1, wherein the at least one electric motor is a DC electric motor.

9. The mobile C-arm system of claim 1, further comprising: a controller connected to each of the at least two wheels individually.

10. The mobile C-arm system of claim 9, wherein the controller comprises a control loop configured to regulate a speed of each wheel of the at least two wheels individually.

11. The mobile C-arm system of claim 1, further comprising:
    a steering configured to pivot the at least three wheels about a vertical axis,
    wherein the steering is configured to actuate each of the at least three wheels individually.

12. The mobile C-arm system of claim 11, wherein the steering is lockable individually for each wheel of the at least three wheels.

13. The mobile C-arm system of claim 12, wherein the at least three wheels are lockable continuously.

14. The mobile C-arm system of claim 12, wherein the at least three wheels are lockable at discrete angular increments.

15. The mobile C-arm system of claim 11, wherein the steering comprises a girth gear unit.

16. The mobile C-arm system of claim 1, further comprising: a power supply for the at least two wheels.

17. The mobile C-arm system of claim 16, wherein the power supply comprises a battery, a fuel cell, or the battery and the fuel cell.

18. The mobile C-arm system of claim 16, further comprising: a charging apparatus for the power supply.

19. The mobile C-arm system of claim 18, wherein the charging apparatus is configured for contactless charging of the power supply.

20. The mobile C-arm system of claim 18, wherein the charging apparatus is configured to charge the power supply by a cable connection.

* * * * *